US012642562B2

(12) United States Patent
Herrmann

(10) Patent No.: US 12,642,562 B2
(45) Date of Patent: Jun. 2, 2026

(54) TECHNIQUE FOR DETERMINING A TRAJECTORY DEFINED BY AN ELONGATED MEMBER PLACED IN BONE

(71) Applicant: Stryker European Operations Limited, Carrigtwohill (IE)

(72) Inventor: Florian Herrmann, Schwanau (DE)

(73) Assignee: Stryker European Operations Limited, Carrigtwohill (IE)

( * ) Notice: Subject to any disclaimer, the term of this patent is extended or adjusted under 35 U.S.C. 154(b) by 379 days.

(21) Appl. No.: 18/204,636

(22) Filed: Jun. 1, 2023

(65) Prior Publication Data

US 2023/0389963 A1 Dec. 7, 2023

(30) Foreign Application Priority Data

Jun. 2, 2022 (EP) .................................... 22177067

(51) Int. Cl.
*A61B 17/70* (2006.01)
*A61B 17/02* (2006.01)

(52) U.S. Cl.
CPC ...... *A61B 17/7002* (2013.01); *A61B 17/7019* (2013.01); *A61B 2017/0256* (2013.01)

(58) Field of Classification Search
CPC ............ A61B 17/7002; A61B 17/7019; A61B 2017/0256
USPC ......................................................... 700/11
See application file for complete search history.

(56) References Cited

U.S. PATENT DOCUMENTS

| | | | |
|---|---|---|---|
| 7,840,254 B2 | 11/2010 | Glossop | |
| 8,764,763 B2 | 7/2014 | Wong et al. | |
| 9,549,744 B2 | 1/2017 | Pommer et al. | |
| 2006/0173291 A1* | 8/2006 | Glossop ................ | A61B 90/39 |
| | | | 600/424 |
| 2007/0270896 A1 | 11/2007 | Perez-Cruet | |
| 2015/0045796 A1* | 2/2015 | Barsoum ................ | A61B 17/16 |
| | | | 606/86 R |
| 2017/0165008 A1* | 6/2017 | Finley .................. | A61B 6/4441 |
| 2019/0000564 A1 | 1/2019 | Navab et al. | |
| 2019/0262076 A1 | 8/2019 | Brown | |
| 2020/0197105 A1 | 6/2020 | Wu | |
| 2020/0275904 A1 | 9/2020 | Gharib et al. | |
| 2020/0323566 A1* | 10/2020 | Geist .................. | A61B 17/8875 |
| 2021/0085268 A1* | 3/2021 | Alexandroni .......... | A61B 90/39 |
| 2022/0110701 A1* | 4/2022 | Crawford .............. | A61B 34/76 |

FOREIGN PATENT DOCUMENTS

| | | |
|---|---|---|
| EP | 3797724 A1 | 3/2021 |
| WO | 2020056086 A1 | 3/2020 |
| WO | 2022079715 A1 | 4/2022 |

* cited by examiner

*Primary Examiner* — Md Azad
(74) *Attorney, Agent, or Firm* — Howard & Howard Attorneys PLLC

(57) ABSTRACT

A computer-implemented technique of determining a trajectory defined by a guide wire or other elongated member is presented. A method implementation of the technique in one variant comprises obtaining image data representative of a guide wire placed in a bone, processing the image data to determine an extension of the guide wire, and selecting a portion of the guide wire extension. The method further comprises determining, from the selected portion of the guide wire extension, trajectory data indicative of a guide wire-defined trajectory.

20 Claims, 11 Drawing Sheets

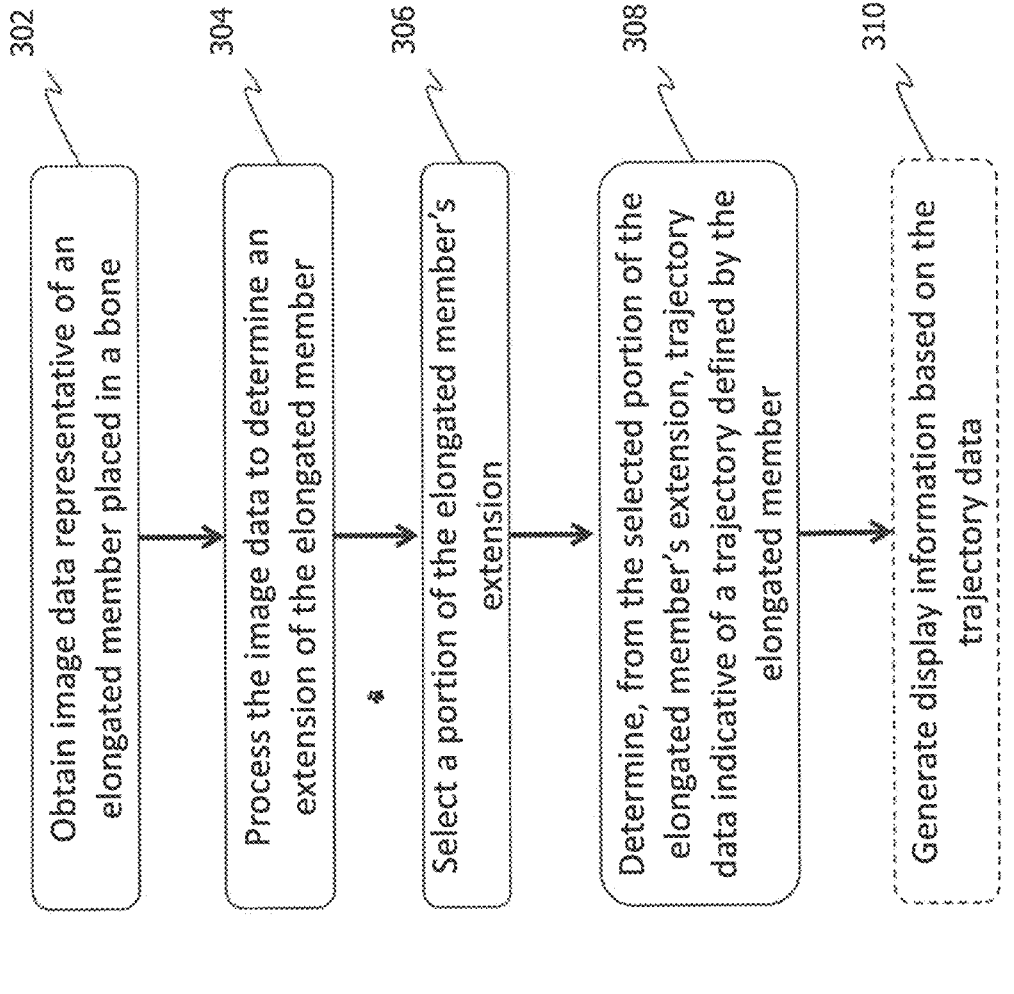

300

302 Obtain image data representative of an elongated member placed in a bone

304 Process the image data to determine an extension of the elongated member

306 Select a portion of the elongated member's extension

308 Determine, from the selected portion of the elongated member's extension, trajectory data indicative of a trajectory defined by the elongated member 310 Generate display information based on the trajectory data

Fig. 3

TECHNIQUE FOR DETERMINING A TRAJECTORY DEFINED BY AN ELONGATED MEMBER PLACED IN BONE

PRIORITY CLAIM

This application claims priority under 35 U.S.C. § 119 to European Patent Application No. 22177067.0, filed Jun. 2, 2022, the entire contents of which are hereby incorporated by reference.

TECHNICAL FIELD

The present disclosure generally relates to the field of computer-assisted surgery. In particular, a computer-implemented technique for determining a trajectory defined by an elongated member placed in bone is presented. In some variants the trajectory is determined for visualization or verification purposes. The technique presented herein can be practiced in the form of a method, a computer program product and an apparatus.

BACKGROUND

Many surgical procedures rely on the placement of a guide wire or other elongated member in bone. In spine surgery, for example, there exist (e.g., minimally invasive) procedures in which the surgeon cannot see an entry point of a pedicle screw in bone. To properly guide the pedicle screw to a desired bone entry point, a guide wire may be temporarily placed in the bone at the desired location. The guide wire may then receive a cannulated pedicle screw and guide the pedicle screw to the desired entry point. In many surgical scenarios, a proper screw trajectory into the bone is equally of importance. In spine surgery, for example, an improper screw trajectory can lead to so-called breaching (and, e.g., to a damaging of the spinal cord). Guide wires can also be employed in such scenarios to define the angle, and thus the trajectory, under which a cannulated screw is inserted into bone.

Guide wire-based surgical procedures transfer the importance of proper screw placement to the precision of the initial guide wire placement procedure. For this reason, it is common to perform an imaging step after guide wire placement to verify that the guide wire has been placed at the desired bone entry point and defines the desired screw trajectory. A proper analysis of the resulting image data is critical for a success of the following screw placement procedure. Of course, the placement of other elongated members in bone may likewise need to be analyzed via an imaging procedure. Such other elongated members may be comprised by so-called bone feelers, pointers, and similar members.

It has been found that image data analysis is associated with a high cognitive load on the surgeon and consumes significant mental resources. For example, the quality of intra-operatively acquired image data is often low in view of time constraints and to reduce radiation exposure, which makes it more difficult for the surgeon to properly identify a guide wire or other elongated member in the image data. Also the appearance of the visualized image data (e.g., in the case of a two-dimensional projection image) can result in cognitive challenges when having to verify a trajectory defined by an elongated member. Image data analysis becomes even more challenging in the case of low bone density (e.g., for older patients).

Evidently, any misplaced guide wire results in a significant safety risk for the patient. In spine surgery, for example, an improper guide wire-defined trajectory can lead to breaching and other severe health damages. Similar issues arise in the context of other elongated members being misplaced in bone.

SUMMARY

There is a need for computer-implemented technique that permits an efficient determination of a trajectory defined by an elongated member placed in bone.

According to a first aspect, a computer-implemented method of determining a trajectory defined by an elongated member is presented. The method comprises obtaining image data representative of an elongated member placed in a bone, processing the image data to determine an extension of the elongated member, and selecting a portion of the extension of the elongated member. The method further comprises determining, from the selected portion of the extension of the elongated member, trajectory data indicative of a trajectory defined by the elongated member.

The elongated member may at least partially or fully be flexible. In this case, the image data may be indicative of one or more bent portions of the elongated member. Additionally, or in the alternative, the elongated member may at least partially or fully be rigid.

In some variants, the elongated member is, or comprises, a guide wire, which typically is flexible along its entire extension. In other variants, the elongated member is, or is comprised by, a bone feeler (e.g., a pedicle feeler), which typically comprises a flexible section to be inserted in a bone opening and a rigid gripping portion. In still other variants, the elongated member is, or is comprised by, a pointer, which typically is a fully rigid tool that may be inserted into a bone opening. In still further variants, the elongated member is, or is comprised by, a depth gauge, which typically comprises a rigid measuring section that is to be inserted into a bone opening.

The selected portion of the extension of the elongated member may comprise two or more points along the extension. The selected portion of the extension may substantially be linear. It may for example be defined by two spaced-apart points or a number of successive points along the extension. The selected portion of the extension may define an axis of the elongated member in bone.

The trajectory may substantially be linear. The trajectory may be indicative of how a surgical implant, such as a cannulated screw, will be guided via the elongated member towards or into bone. In other variants, the trajectory may be indicative of a direction in which the elongated member has been inserted into the bone.

The trajectory data may comprise data defining a line or a line segment in space. In some implementations, the trajectory data may define the line or line segment in a coordinate system of the image data. The line or line segment may be determined to be co-linear with the selected portion of the extension of the elongated member.

In one variant, processing the image data comprises segmenting the image data to determine first image information representative of the elongated member. To this end, image analysis techniques can be used. If, for example, the image data are computer tomography (CT) data, the segmenting may be based on an analysis of the Hounsfield values comprised by the CT data. The portion of the extension may be selected based on the first image information.

Processing the image data may comprise determining an endpoint of the elongated member in the bone. In some variants, the endpoint is derived from the first image information. The endpoint may be determined in a coordinate system of the image data. The selected portion of the extension may be based on the endpoint of the elongated member. For example, the selected portion of the extension may start at the endpoint. The selected portion of the extension may comprise the endpoint and stretch over a length of the extension from that endpoint. The length may be defined by a user or automatically. The trajectory data may be determined based on the length of the extension from the endpoint. The trajectory data may comprise the endpoint.

The method may comprise segmenting the image data to determine second image information representative of a bone surface. In such a case, selecting the portion of the extension of the elongated member may comprise determining an intersection between the bone surface and the extension. The selected portion of the extension may not substantially extend beyond the bone surface. In some variants, the length of the extension from the endpoint may be determined based on the intersection between the bone surface and the extension. As an example, the intersection may define the other endpoint of the selected portion of the extension.

The method may comprise generating display information based on the trajectory data. The display information may be configured to visualize at least one of the trajectory of the elongated member and the endpoint of the elongated member in the bone. In some implementations, the display information is configured to visualize at least one of (i) the trajectory and (ii) the endpoint in the bone superimposed on the image data that were processed to determine the extension of the elongated member. Alternatively, the superposition may take place relative to other (e.g., pre-operatively acquired) image data representative of the bone.

The method may comprise processing the image data based on the trajectory data. The display information may be indicative of (e.g., visualize) the processed image data. In some implementations, processing of the image data comprises at least one of orienting the image data (e.g., dependent on the trajectory) and zooming into the image data (e.g., with an image center defined by an endpoint of the elongated member).

The method may comprise determining, based on the trajectory data, a cylindrical volume centered relative to the trajectory. In one variant, the elongated member serves for placement of a cannulated screw (e.g., for guiding a pedicle screw). In such a case, the method may comprise determining at least one screw parameter of the cannulated screw. The screw parameter may comprise at least one of a screw length and a screw diameter. The cylindrical volume may be determined based on the at least one screw parameter (e.g., a diameter of the cylindrical volume may be selected to equal a screw diameters). If the screw is a pedicle screw, the screw parameter may be determined to avoid breaching.

The trajectory defined by the trajectory data may extend beyond the selected portion of the extension of the elongated member. As an example, the trajectory data may define a line or a line segment that is longer than the selected portion of the extension of the elongated member.

In some surgical procedures, two or more elongated members are utilized. In such cases, the image data may be representative of at least one other elongated member placed in the, or another, bone. The method may then comprise processing the image data to determine an extension of the other elongated member, selecting a portion of the extension of the other elongated member, and determining, from the selected portion of the extension of the other elongated member, further trajectory data indicative of a trajectory of the other elongated member. The method may further comprise determining a relationship between the trajectories of the elongated members. The relationship may comprise at least one of a distance relationship and an angular relationship Also provided is a computer program product comprising program code portions to perform the steps of the method presented herein when the computer program product is executed by a processor. The computer program product may be stored on a computer-readable recording medium.

Also provided is an apparatus for determining a trajectory defined by an elongated member. The apparatus is configured to obtain image data representative of an elongated member placed in a bone, to process the image data to determine an extension of the elongated member, and to select a portion of the extension of the elongated member. The apparatus is further configured to determine, from the selected portion of the extension of the elongated member, trajectory data indicative of a trajectory defined by the elongated member.

The apparatus may configured to perform any of the method steps presented herein. The apparatus may comprise one or more processors and may be realized as a computing device.

According to a further aspect, a computer-implemented method of determining an endpoint defined by an elongated member is presented. The method comprises obtaining image data representative of an elongated member placed in a bone and processing the image data to determine an endpoint of the elongated member in bone. The endpoint thus determined may be used to check if the elongated member has been properly placed (e.g., in accordance with a predefined surgical plan indicative of a target endpoint). The check may be performed visually by a surgeon or automatically.

BRIEF DESCRIPTION OF THE DRAWINGS

Further details, advantages and aspects of the present disclosure will become apparent from the following embodiments taken in conjunction with the drawings, wherein:

FIG. 3 illustrates a flow diagram of a method of determining trajectory data;

DETAILED DESCRIPTION

The following description is specifically related to spinal interventions. It will be apparent that the present disclosure can also be implemented in other surgical contexts. Moreover, while the following description focuses on guide wires as exemplary elongated members, it will be apparent that the elongated members may also have different configurations. For example, the elongated members may be realized as, or be comprised by, bone feelers (e.g., pedicle feelers), pointers or depth gauges. Evidently, all these elongated members define trajectories.

Spinal interventions have become a widespread surgical treatment and are currently performed either manually by a surgeon, automatically by a surgical robot, or semi-automatically by a surgeon using robotic assistance. To guarantee proper surgical results, spinal interventions require surgical planning and intra-operative imaging to verify that the ongoing surgical procedure conforms to the surgical plan.

Figure 1A:
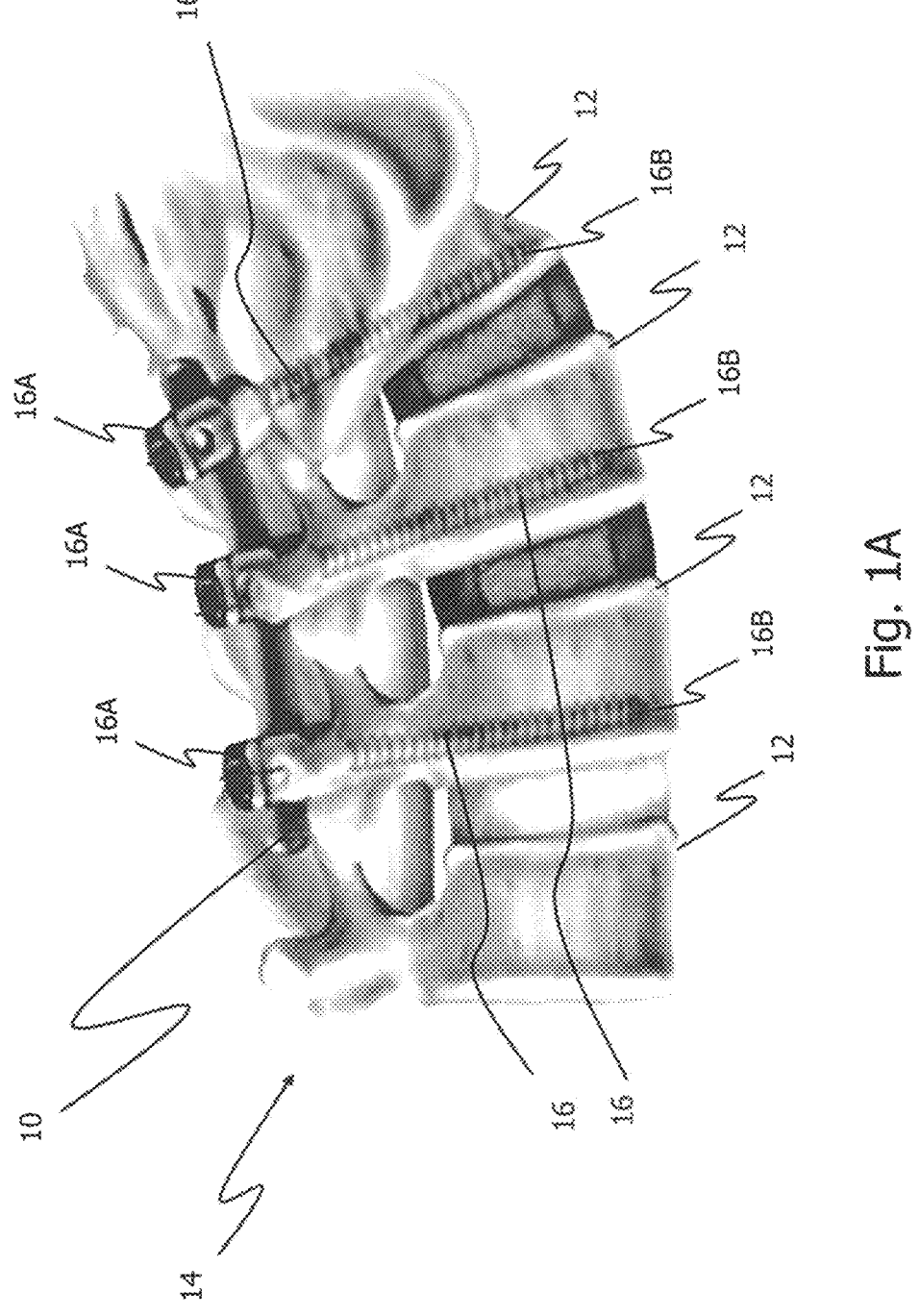
FIG. 1A schematically illustrates a spinal rod stabilizing multiple vertebrae.

With reference to FIG. 1A, in some spinal interventions a pre-formed rod 10 is implanted to stabilize two or more vertebrae 12 of a patient's spine 14. The rod 10 may be pre-formed prior to its implantation according to a planned shape of the spine 14. After implantation, the rod 10 stabilizes the spine in accordance with the planned shape.

FIG. 1A shows that the pre-formed rod 10 is coupled to the vertebrae 12 using pedicle screws 16. Each pedicle screw 16 has a first end 16A attached to the rod 10 and an opposite second end 16B anchored in a particular vertebra 12 at a planned bone entry point and oriented along a planned screw extension. The extension of a particular pedicle screw 16 in a particular vertebra 12 may be planned pre-operatively based on pre-operatively acquired image data of the spine 14. In other scenarios, pedicle screw placement is planned by intra-operatively.

Figure 1B:
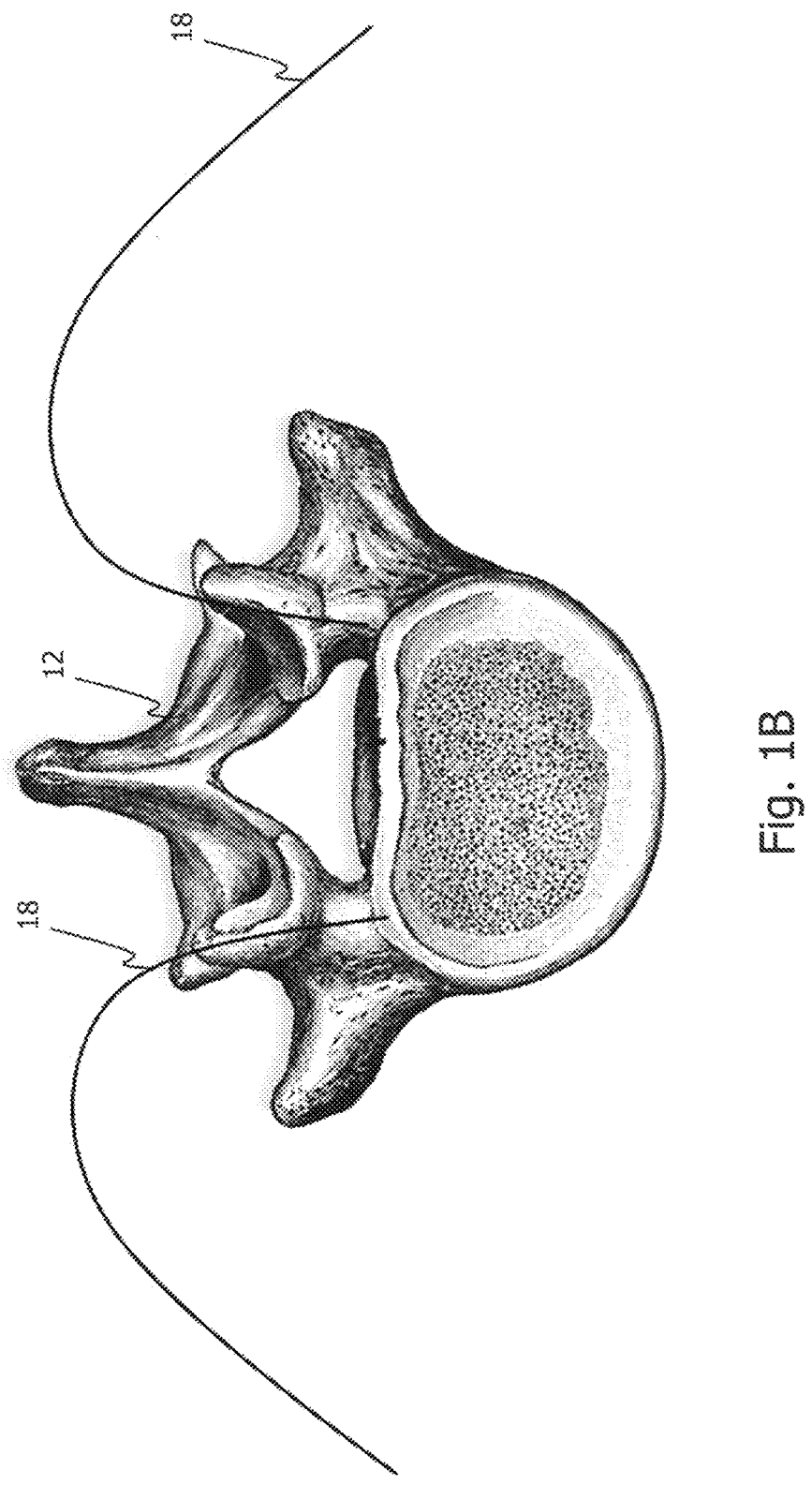
FIG. 1B schematically illustrates the placement of guide wires as exemplary elongated members in a vertebra.
Figure 1C:
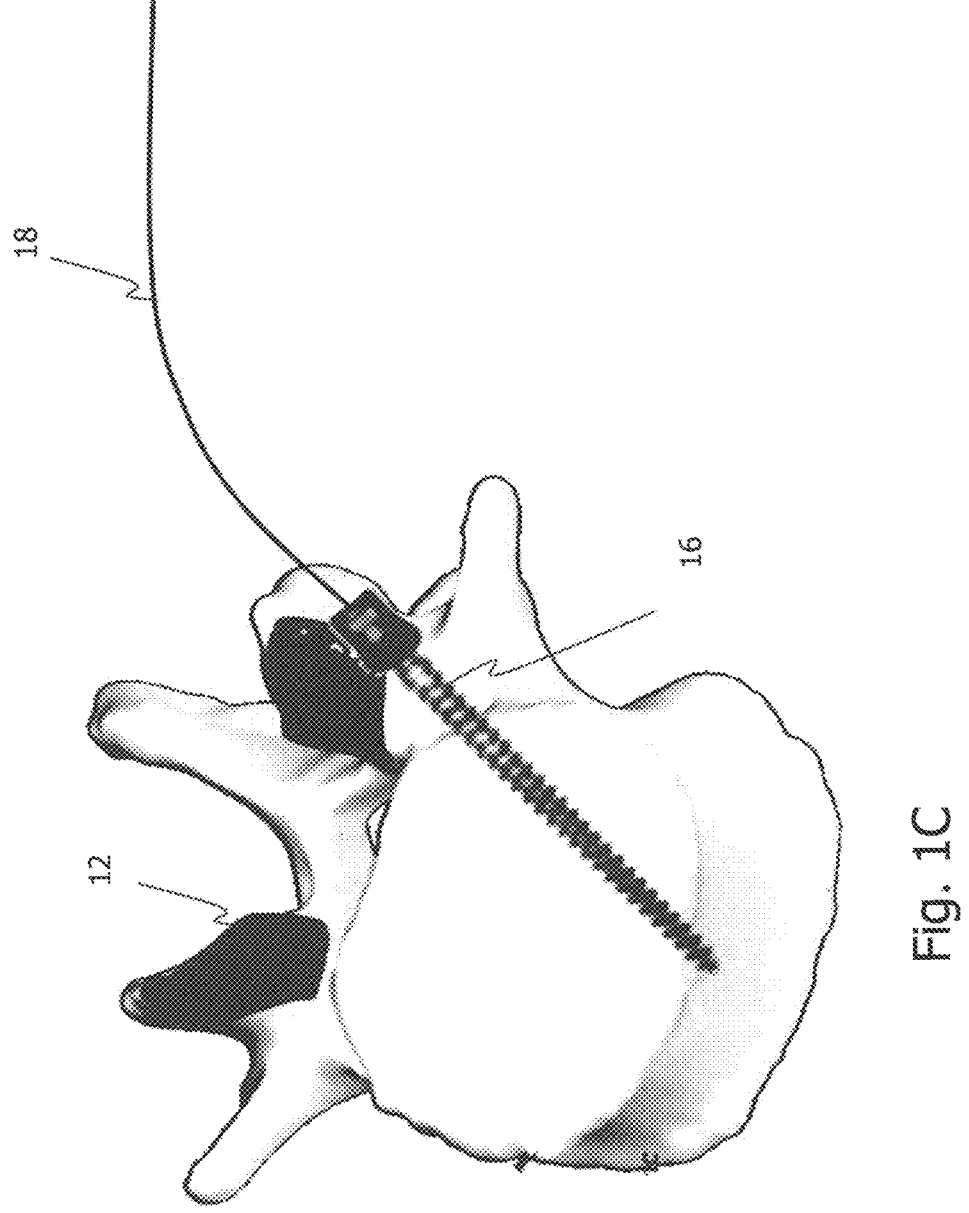
FIG. 1C schematically illustrates pedicle screw placement using a guide wire.

Pedicle screw placement can be facilitated using guide wires 18 as exemplary elongated members, as illustrated in FIG. 1B. The guide wires 18 (such as Kirschner wires, also called K wires) help to guide cannulated pedicle screws 16 to their desired bone entry points and along desired trajectories, as illustrated in FIG. 1C.

Once the guide wires 18 have been placed in one or more vertebrae 12, possibly using surgical navigation techniques, image data are acquired intra-operatively for verification purposes. Based on the image data, the surgeon or a software routine can check if the guide wires 18 have been properly placed (e.g., in accordance with a planned pedicle screw placement). The guide wires 18 are flexible members that can be bent as needed during the surgical intervention. As such, also the image data may be indicative of one or more bent portions of the guide wires 16 outside the bone.

Figure 2B:
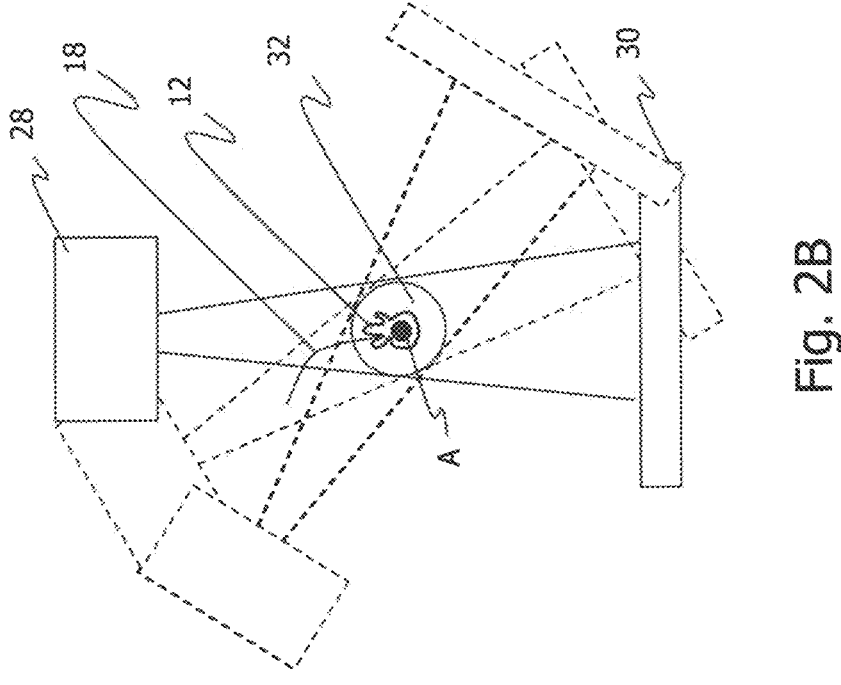
FIGS. 2A & B schematically illustrate a surgical system with imaging capabilities.
Figure 2A:
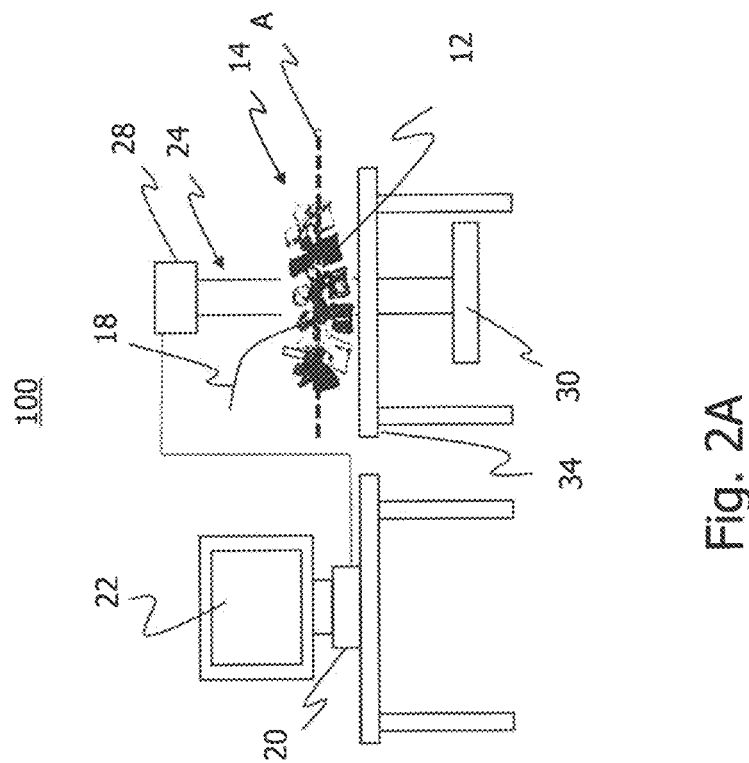

FIG. 2A schematically illustrates an exemplary surgical system 100 that is configured to determine trajectory data indicative of a trajectory defined by a guide wire 18 (or other elongated member). The system 100 may use the trajectory data for visualization, verification, navigation or other purposes. The surgical system 100 illustrated in FIG. 2A comprises an apparatus 20 configured to determine the trajectory data. In some variants, the apparatus 20 may be part of a surgical navigation system.

In FIG. 2A, the apparatus 20 is realized as a locally deployed computer system comprising one or more processors and memory storing program code for controlling operation of the one or more processors. Alternatively, the apparatus 20 may be realized in the form of a remote server or in the form of cloud computing resources. In other variants, the apparatus 20 may take the form of a tablet computer or other mobile device.

The system 100 of FIG. 2A comprises an output device 22 configured to output information that has been derived based the trajectory data determined by the apparatus 20 (e.g., for information, verification, modification or confirmation purposes, or for navigation purposes). In the scenario of FIG. 2A, the output device 22 is a display device configured to visually output the trajectory data or information derived therefrom. In other variants, the output device 22 may be configured to (e.g., additionally or alternatively) output one or more of acoustic and haptic information. The output device 22 may be realized as, or comprise, a computer monitor, an augmented reality device (e.g., a head-mounted display), a loudspeaker, an actuator configured to generate haptically detectable information, or a combination thereof.

The apparatus 20 is configured to determine the trajectory data from input data, as will now be explained in greater detail with reference to the flow diagram 300 of FIG. 3. The input data comprise image data obtained on the basis of one or more surgical imaging techniques. For this reason, the surgical system 100 of FIG. 2A further comprises an imaging apparatus 24 configured to intra-operatively acquire image data of one or more vertebrae 12 of the patient's spine 14 with one or more guide wires 18 being placed therein. In step 302 of FIG. 3, the image data acquired by the imaging apparatus 24 are obtained by the apparatus 20 (e.g., via a data interface).

In the exemplary scenario illustrated in FIG. 2A, the imaging apparatus 24 is a C-arm with cone beam computer tomography (CBCT) imaging capabilities. In other scenarios, the imaging apparatus 24 is a conventional CT scanner that generates slice images, an EOS scanner or an X-ray apparatus. In still further scenarios, the imaging apparatus 24 utilizes a magnet resonance- (MR-) based imaging technique.

The exemplary CBCT-based imaging apparatus 24 of FIG. 2A comprises a radiation source 28 configured to generate a cone-shaped beam of radiation. Moreover, the imaging apparatus 24 has a flat-panel detector 30 configured to detect the radiation beam projected by the radiation source 28 through one or more of the vertebrae 12 with the one or more guide wires 18 being placed there. The detector 30 is configured to generate image data representative of two-dimensional projection images of the vertebrae 12 and the guide wires 18. As illustrated in FIG. 2B, such projection images of an imaged volume 32 containing the vertebrae 12 and the guide wires 18 are taken at two more angular orientations of the C-arm relative to an imaginary longitudinal axis A of the vertebrae 12. From the resulting two-dimensional images, in some variants three-dimensional image data are derived using reconstruction (e.g., back-projection) techniques. The reconstruction may be performed either by the imaging apparatus 24 itself or by the apparatus 20.

Figure 4A:
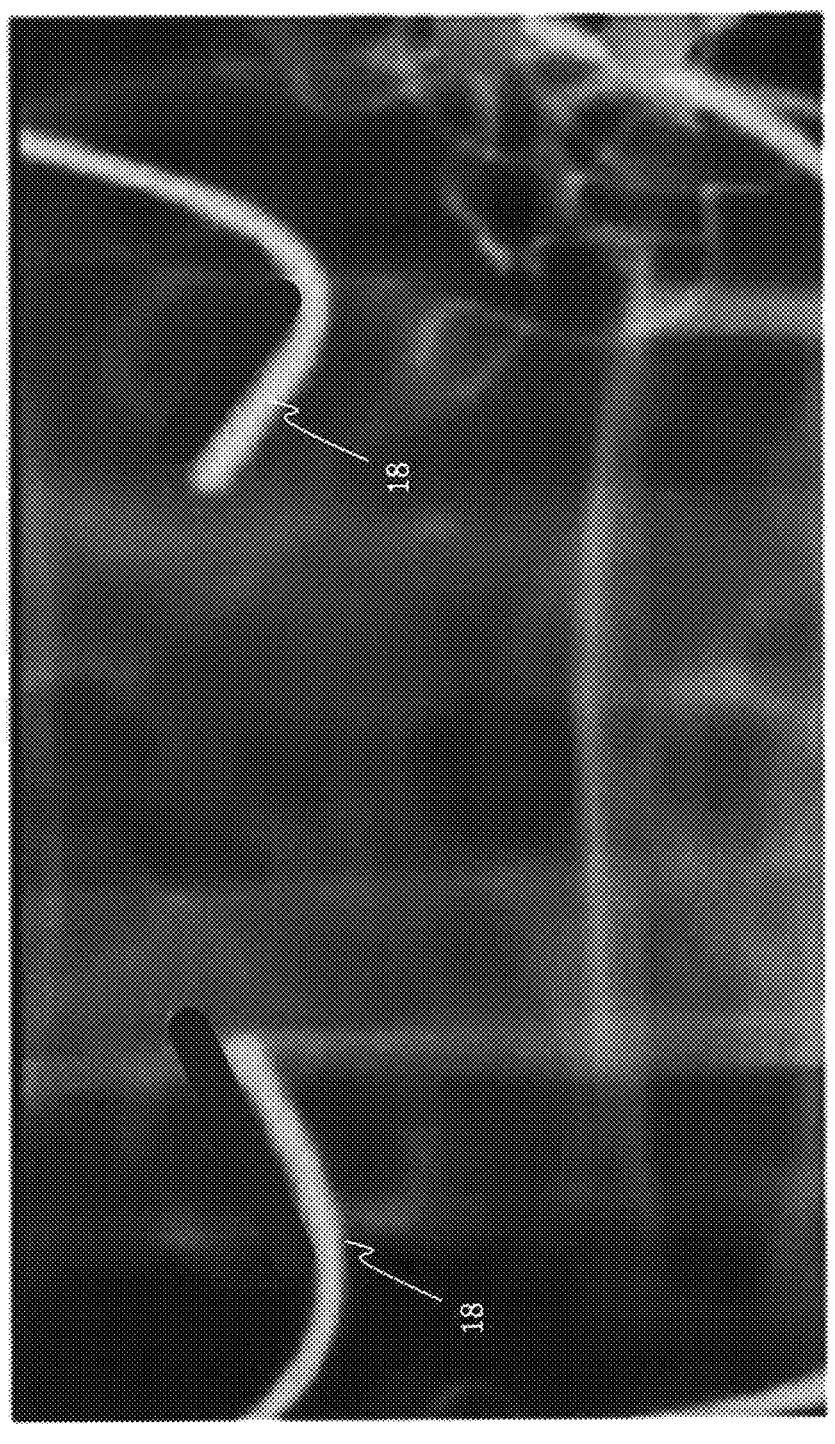
FIGS. 4A & B illustrate an exemplary visualization of the trajectory data.

FIG. 4A illustrates exemplary two-dimensional X-ray image data taken from a portion of a patient's spine 14 with two guide wires 18 being placed in a particular vertebra (similar to the surgical scenario illustrated in FIG. 1B). The guide wires 18 are visible as white traces and have a proximal portion with a generally linear, or straight, extension within the vertebra bone and a distal portion with a curved extension outside the vertebra bone. The generally linear proximal portion can be considered to define a guide wire axis (and an insertion trajectory for a cannulated pedicle screw).

As becomes apparent from FIG. 4A, the guide wires 18 cannot be easily identified due to a limited image resolution that was intentionally selected to reduce radiation exposure for the patient and the surgical personnel. As such, the surgeon cannot easily verify that the guide wires 18 are placed and oriented as desired.

Similar challenges may occur upon placement of other elongated members. For example, the surgeon may wish to pre-drill holes in the bone that are to receive the guide wires 18. Pointers, bone feelers or depth gauges may then be temporarily inserted into the holes when a surgeon may wish to confirm or verify the orientation (and/or possibly the depth, e.g., in terms of a later endpoint of a guide wire 18 or an implant) of the holes in image data acquired with such an elongated member being placed therein.

In step 304 of FIG. 3, the image data obtained in step 302 are processed to determine an extension of each guide wire 18 (or other elongated member) in bone. In some implementations, image analysis techniques are applied in step 304 so to determine image information representative of each guide wire 18. An image data segmenting approach may be performed to differentiate each guide wire 18 from surrounding tissue or air. The segmenting may be performed on a per-pixel or per-voxel basis of the underlying image data. In the case of CT image data, the segmenting may be based on an analysis of the Hounsfield values comprised by the CT data since the (typically metallic) guide wires 18 have different Hounsfield values than the surrounding tissue or air.

In some variants, the guide wire extension is determined in the coordinate system of the image data. The guide wire extension may be defined by a two-dimensional or three-dimensional structure (e.g., as a line, area or volume having at least one substantially straight section and at least one substantially curved section, see FIG. 4A).

Once the extension of each guide wire 18 or other elongated member has been determined in step 304, a dedicated portion of that extension is selected in step 306. In some variants, step 306 targets at identifying the at least a part of the proximal guide wire extension portion that defines a later pedicle screw trajectory into the bone. The portion of the guide wire extension selected in step 304 may entirely, or at least substantially, lie within the bone. The selected portion of the guide wire extension may substantially be linear. On the other hand, the typically curved distal portion of the guide wire extension outside the bone may not be selected (e.g., may in essence be deselected in step 306).

The selected portion of the guide wire extension may be represented as a two-dimensional or three-dimensional structure in the coordinate system of the image data. The selected portion of the guide wire extension may be defined as a set of pixels or voxels or as a geometric function.

There exist various possibilities how to select the guide wire extension portion in step 306. For example, processing the image data in step 304 may comprise determining an endpoint of each guide wire 18 in the vertebra bone. The endpoint can be derived from the segmented image information and in the coordinate system of the image data. The selected portion of the guide wire extension may start at the guide wire endpoint and may stretch along a length of the guide wire extension from that endpoint. The length may be defined by a user or automatically. In some variants, a user may define the length (e.g., of 1 cm), so that the selected guide wire extension portion stretches from the guide wire endpoint in the vertebra bone to a second endpoint identified by the user-defined length along the guide wire extension.

For an automatic length determination, the image data may be segmented to determine image information representative of a bone surface (e.g., based on an analysis of the Hounsfield values in CT image data). In such a case, selecting the portion of the guide wire extension in step 306 may comprise determining an intersection between the bone surface and the guide wire extension as determined in step

304. The length of the guide wire extension from the guide wire endpoint may automatically be determined based on the intersection between the bone surface and the guide wire extension. In particular, the intersection may define the other endpoint of the selected portion of the guide wire extension, so that the selected guide wire extension portion stretches from the guide wire endpoint in the vertebra bone at least to the intersection of the guide wire extension with the vertebra bone surface. In case it is found that the guide wire does not extend deep enough into bone, the selected portion of the guide wire extension may go beyond the intersection of the guide wire extension with the bone surface.

The method illustrated in FIG. 3 then proceeds to determining, from the portion of the guide wire extension selected in step 304, trajectory data indicative of a trajectory defined by the guide wire 18 or other elongated member (see step 308 in FIG. 3). The trajectory data may define a line or line segment representative of the guide wire-defined trajectory, for example in a coordinate system of the image data. The line or line segment may be determined to be co-linear with the selected portion of the guide wire extension. The trajectory data may take the form of a geometric definition (e.g., in the form of a linear function) or may take the form of set of dedicated pixels or voxels in the image data. In some variants, the trajectory data may be identical to, or representative of, the selected portion of the guide wire extension. In some variants, a length of the guide wire-defined trajectory as defined in the trajectory data may be the same as, or different from, the length of the selected portion of the guide wire extension.

The trajectory data may in some variants comprise the guide wire endpoint in bone. The guide wire endpoint may be included in the trajectory data as part of the guide wire-defined trajectory. Additionally, or in the alternative, the guide wire endpoint may be included as a dedicated point in the trajectory data (e.g., in addition to the guide wire-defined trajectory).

The trajectory data may be used in various ways. For example, the trajectory data, possibly in combination with the bone surface image information, may be used for automatically matching at least one of the guide wire-defined trajectory and the guide wire endpoint with a pre-operative surgical plan. The pre-operative surgical plan may include at least one of an entry point of a pedicle screw into bone, an orientation of the pedicle screw in the bone and an insertion depth of the pedicle screw into bone.

In some variants, the trajectory data may be used by a surgeon to visually match the guide wire-defined trajectory with the pre-operative or an intra-operative plan for pedicle screw placement. In the latter case, the method illustrated in FIG. 3 may comprise an optional step 310 of generating display information based on the trajectory data. The display information can take the form of display instructions (e.g., a video signal). The display information may be rendered by the output device 22 illustrated in FIG. 2A.

The display information may be configured to visualize at least one of the guide wire-defined trajectory and the endpoint of the guide wire in the bone. In some implementations, the display information may be configured to visualize the guide wire-defined trajectory superimposed on the image data that were processed to determine the guide wire extension (see FIG. 4B). In other implementations, the display information may be configured to visualize the guide wire-defined trajectory superimposed on other image data representative of the bone. Such other image data may have been pre-operatively acquired. It is also possible to generate display information that visually highlight the guide wire extension as determined in step 304 in the image data (e.g., using a specific colour).

Figure 4B:
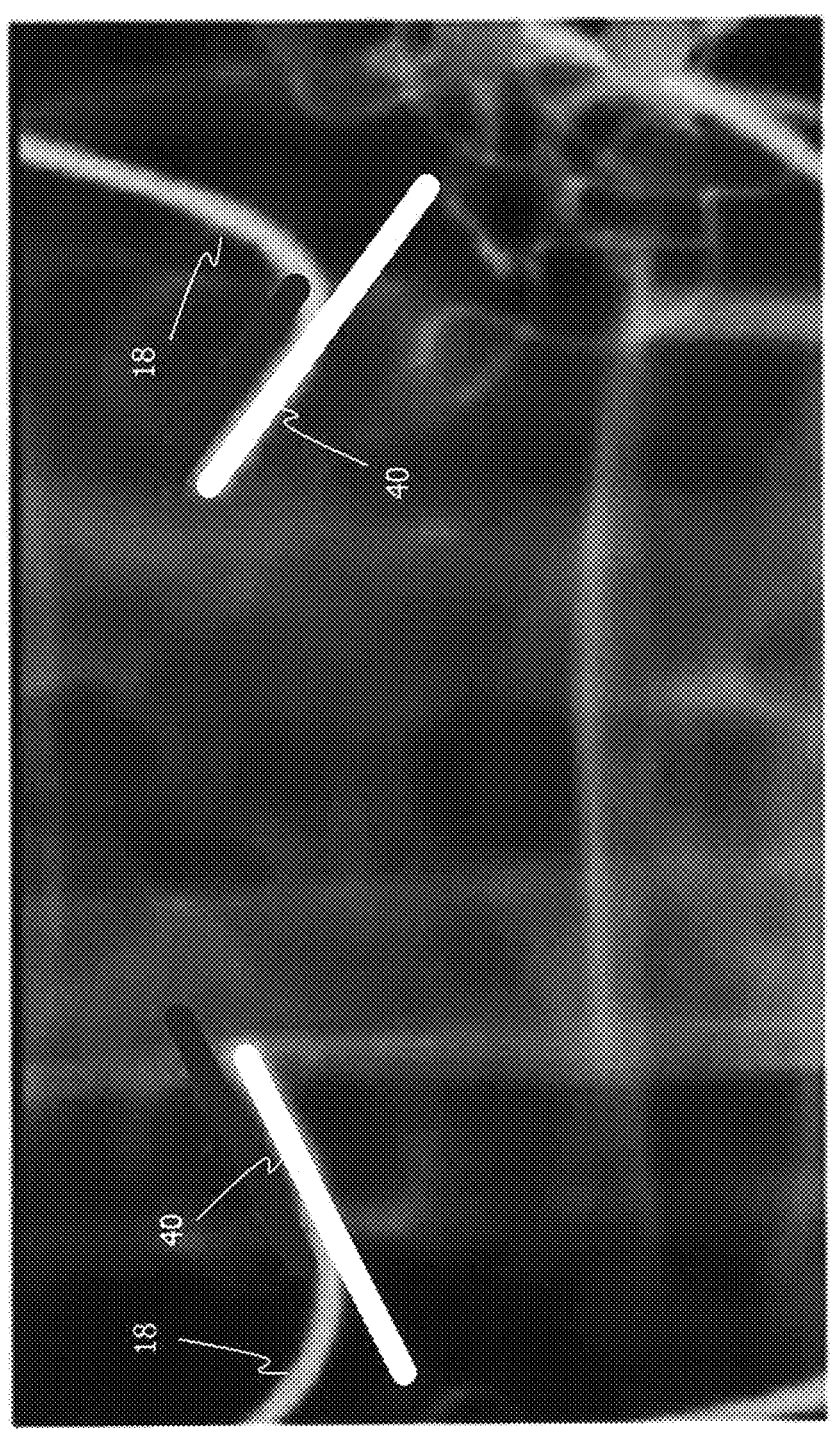

FIG. 4B shows two guide wire-defined trajectories 40 superimposed on the respective guide wire 18 in the image data illustrated in FIG. 4A. The content of FIG. 4B may be rendered on the output device 22 shown in FIG. 2A.

As becomes apparent from FIG. 4B, each superimposed trajectory 40 is located to be co-linear with the portion of the guide wire extension selected in step 306. The length of each visualized trajectory 40 may be selected automatically or may be defined by a user. For example, the guide wire-defined trajectory 40 may be visualized such that it starts at the respective guide wire endpoint in bone and extends beyond the bone surface, as depicted in FIG. 4B.

Figure 5A:
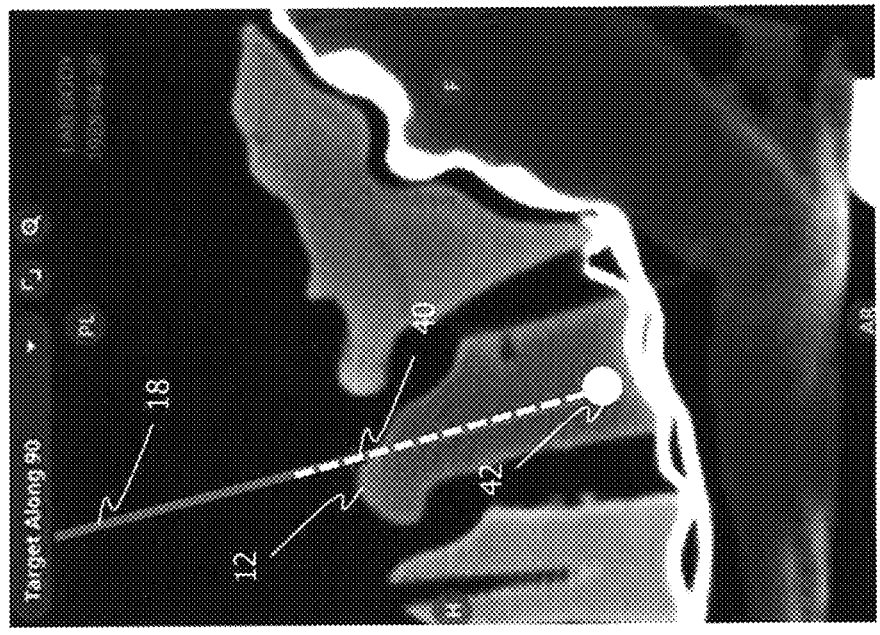
FIGS. 5A & B illustrate further exemplary visualizations of the trajectory data.
Figure 5B:
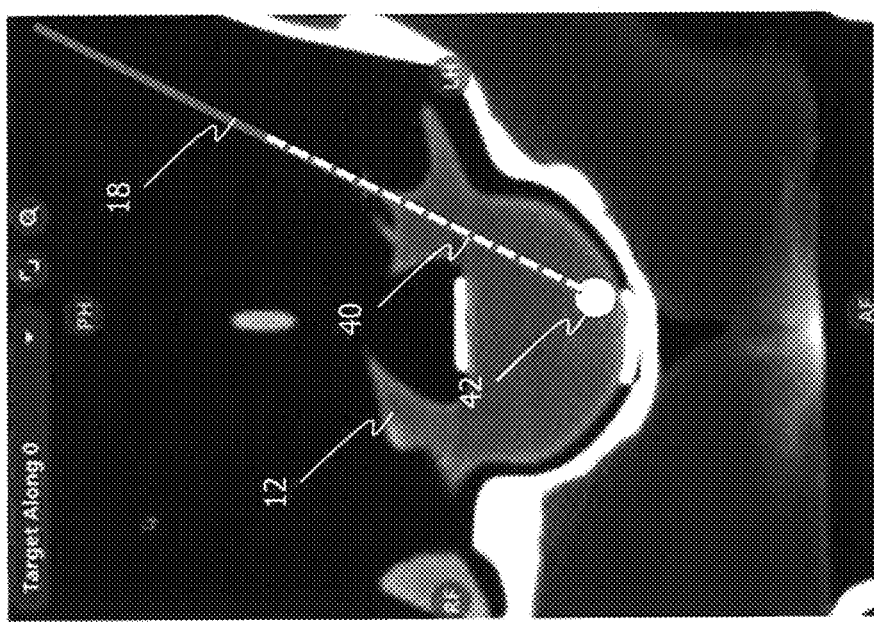

The guide wire endpoint may be visualized using a dedicated icon, as shown in FIGS. 5A and 5B. The content of FIGS. 5A and 5B may be rendered on the output device 22 shown in FIG. 2A.

FIGS. 5A and 5B show two perpendicular cuts through three-dimensional CT image data of a vertebra 12 in the transversal (i.e., axial) plane and the saggital plane, respectively.

The trajectory 40 is represented by a dashed line. An associated endpoint 42 of the guide wire is represented by an icon in the form of a white circle. The surgeon may thus visually analyse the trajectory 40 to check if the guide wire is properly oriented relative to the vertebra 12. Moreover, by inspecting the guide wire endpoint 42 the surgeon can check that the guide wire is securely rooted in the vertebra 12. Both checks are of significant importance to a proper pedicle screw placement in the surgical steps that follow.

The image data obtained in step 302 may be processed based on the trajectory data determined in step 308, and the processed image data may then be used for generating the display information in step 310. In particular, the display information may comprise the processed image data. As an example, in case the trajectory data comprise the guide wire endpoint 42, processing of the image data may comprise zooming into the image data in a region of one or both of the guide wire-defined trajectory 40 and the guide wire endpoint 42. The display information may be generated so as to include (e.g., only) the zoomed-in region of the image data.

Additionally, or in the alternative, processing of the image data based on the trajectory data may comprise centering the image data relative to one or both of the guide wire-defined trajectory 40 and the guide wire endpoint 42. The display information may be generated so as to include the centered image data. As a further alternative, or in addition, processing of the image data based on the trajectory data may comprise orienting the image data to include one or both of the trajectory 40 and the guide wire endpoint 42. In some variants, the image data may be oriented such that the trajectory 40 extends vertically or horizontally when being visualized. In such or other variants, the image data may be oriented such that the trajectory 40 is oriented relative to a saggital or axial view. The display information may be generated so as to include the oriented image data (as illustrated by the two cuts in FIGS. 5A and 5B).

Figure 6:
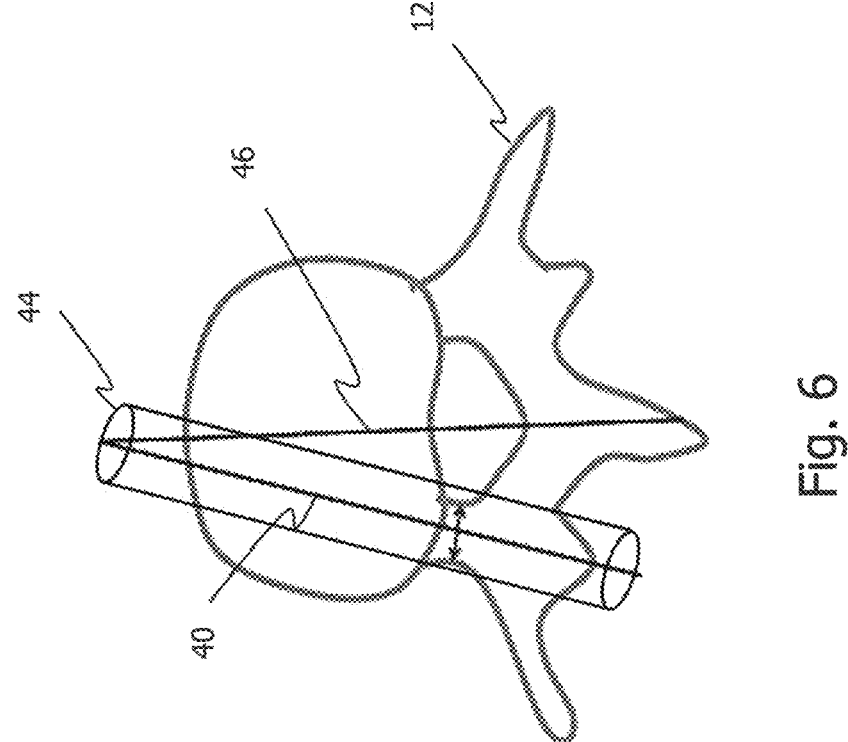
FIG. 6 schematically illustrates exemplary uses of the trajectory data.

Based on the trajectory data, a cylindrical volume 44 may be determined that is centered relative to the guide wire-defined trajectory 40, as illustrated in FIG. 6. The cylindrical volume 44 may be virtually (or visually) superimposed on bone surface information for breaching analysis, as also illustrated in FIG. 6. In more detail, the cylindrical volume may have a diameter that corresponds to a diameter of a pedicle screw. The screw diameter may automatically be determined (e.g., selected or adjusted) such that breaching is avoided. In some variants, also a screw length may be automatically determined to avoid breaching, or in view of other constraints.

In the scenario of FIG. 6, the screw diameter initially selected (by the surgeon or in an automatic manner) is too large, resulting in breaching as indicated by a double-headed arrow. The apparatus 20 may output a corresponding warning in case the initial screw diameter was selected by the surgeon. Additionally (or in the alternative in case the initial screw diameter was automatically selected), the apparatus 20 may determine a smaller screw diameter that avoids breaching. Of course, other or alternative screw parameters, such as a screw length, may be determined in a similar manner.

Moreover, based on the trajectory data an angular relationship of the guide wire-defined trajectory 40 relative to a symmetry plane 46 of the vertebra 12 may be determined, as also illustrated in FIG. 6. The angular relationship thus determined may be output (e.g., visualized) to the surgeon. Additionally, or in the alternative, the angular relationship may be compared with one or both of standardized value and a patient-specific value defined in a surgical plan, such as a planned angular relationship of a pedicle screw relative to the symmetry plane 46. A result of the comparison may be output to the surgeon. For example, the apparatus 20 may output a warning if the angular relationship of the trajectory 40 relative to the symmetry plane 46 deviates from the planned angular relationship by more than a threshold amount. Moreover, in a surgical scenario as illustrated in FIG. 1B (i.e., with two guide wires 18 being placed in a particular vertebra 12), it may be determined if the guide wires 18 have the same angular relationship relative to the symmetry plane 46.

Figure 7B:
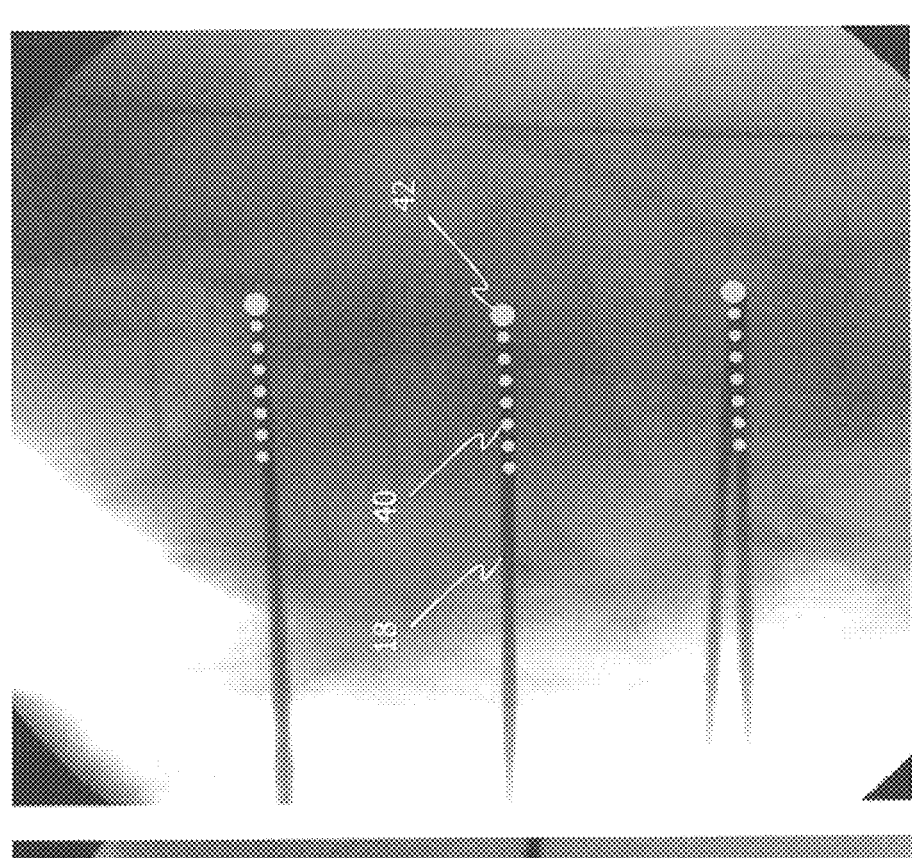
FIG. 7A & B schematically illustrate a visualization of trajectory data for multiple guide wires.
Figure 7A:
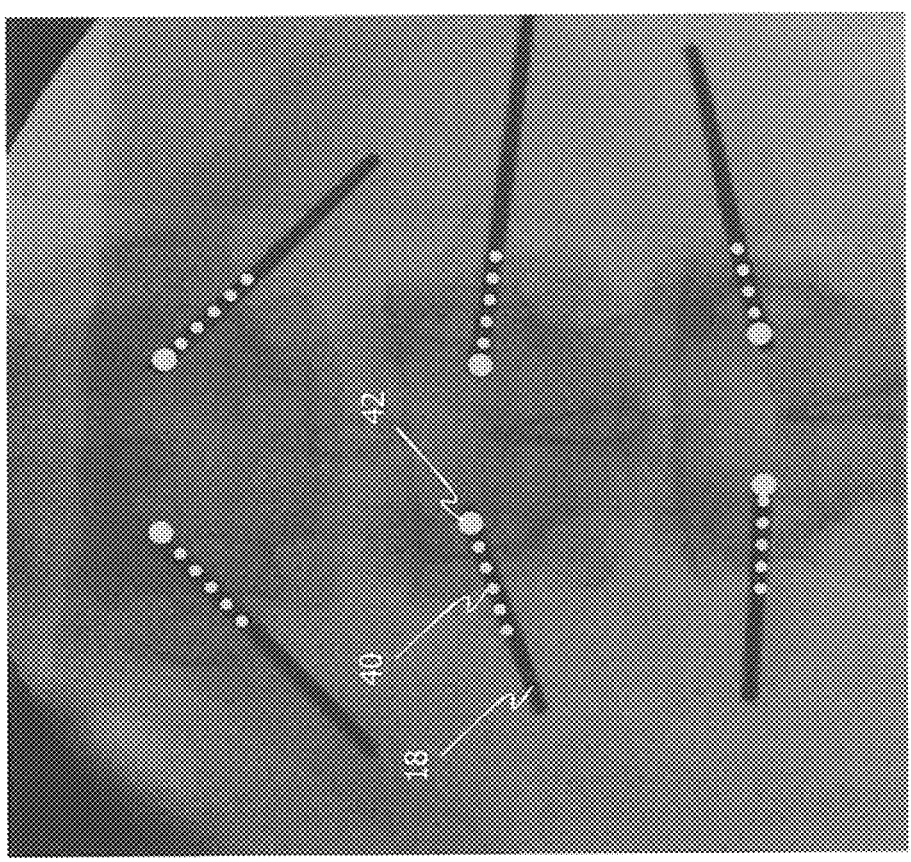

With reference to FIGS. 7A and 7B, the image data obtained in step 302 may be representative of multiple guide wires 18 placed in bone. In more detail, two guide wires 18 may be placed in each vertebra 12 in the manner illustrated in FIG. 1B. FIGS. 7A and 7B show two perpendicular image data projections of three vertebra 12 in the coronal plane and the saggital plane, respectively.

In a scenario with multiple guide wires 18 being placed in bone, step 304 of FIG. 3 comprises processing the image data obtained in step 302 to separately determine the extension of each guide wire. In an image data segmenting procedure, separate image information (e.g., in terms of pixels or voxels) may thus be determined per guide wire 18. In a similar manner, for each guide wire 18 a portion of the guide wire extension will be selected in step 306 and trajectory data indicative of its trajectory will be determined in step 308. The guide wire trajectories 40 may then be visualized together with the associated endpoints 42 for visual verification purposes. (see FIGS. 7A and 7B).

Additionally, or in the alternative, a relationship between two or more of the multiple trajectories 40 illustrated in FIGS. 7A and 7B may be determined. The relationship may comprise at least one of a distance relationship and an angular relationship, or any other geometric relationship. The relationship thus determined may be output as numerical values, as illustrated in FIG. 8.

Figure 8:
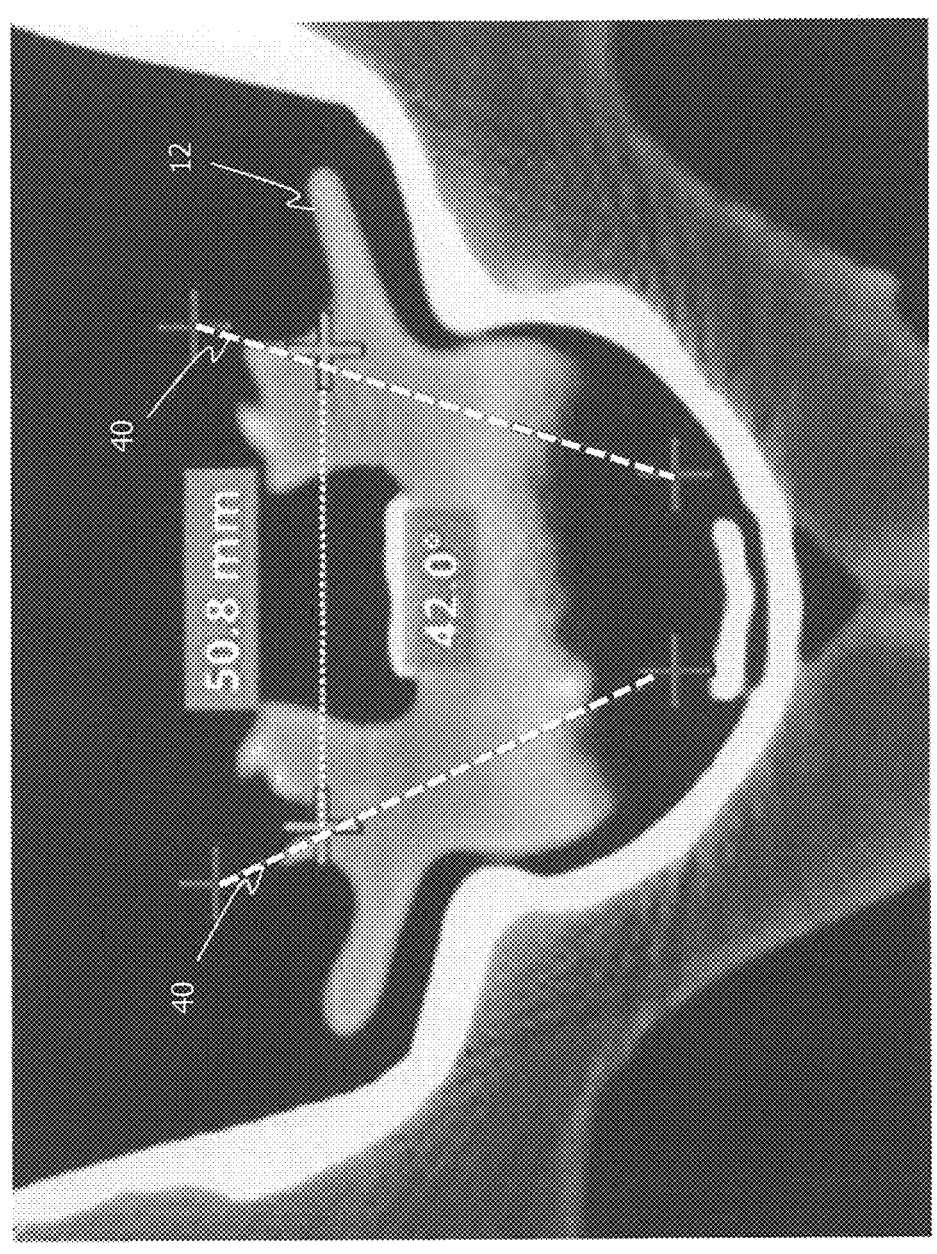
FIG. 8 schematically illustrate the visualization of geometric relationships between two guide wire trajectories.

FIG. 8 is a visualization of CT data similar to FIG. 5A in a scenario in which two guide wires have been placed in a vertebra 12. The trajectories 40 of the two guide wires are visualized and their angular relationship in the transverse plane is automatically determined and output (here:42°). A distance between the two trajectories 40 is automatically determined also, possibly at user-selected positions, and output (here: mm). In some variants, the numerical values thus determined may be compared with corresponding values of a pre-operative surgical plan.

In scenarios as depicted in FIGS. 5A, 5B, 6 and 8, the surgeon may be prompted to adjust the placement of one or more of the guide wires depending on an automated analysis of the trajectory data, optionally in combination with an automated analysis of at least one of the image data (e.g., in terms of bone surface information) and pre-operatively defined planning data (e.g., in terms of a planned bone entry point or a planned orientation of a pedicle screw in bone). In case more than one guide wire has been placed, the one or more guide wires in need of a re-replacement may visually be highlighted, possibly with an indication of the correct positioning.

As has become apparent from the above description of exemplary realizations of the present disclosure, the technique presented herein assists a surgeon or an automated surgical procedure in determining a guide wire-defined trajectory 40 for verification, confirmation, visualization or other purposes. In some implementations, the cognitive load on the surgeon can thus be reduced. In such or other implementations, verification procedures can be automated.

The realizations described above pertain to a computer-assisted technique for determining a guide wire-defined trajectory 40 in the context of the placement of cannulated pedicle screws 16 in vertebrae 12 that are to be stabilized by a pre-formed spinal rod 10 (see FIG. 1A). It will be appreciated that guide wires 18 are used in a large variety of different surgical procedures, so that the guide wire trajectories 40 could alternatively, or additionally, be used in the context of surgical procedures different from pedicle screw placement. Of course, the guide wires 18 are just examples of elongated members configured to be placed in bone.

The invention claimed is:

1. A computer-implemented method of determining a trajectory defined by an elongated member, the method comprising obtaining image data representative of an elongated member placed in a bone;

processing the image data to determine an extension of the elongated member;

segmenting the image data to determine first image information representative of a bone surface;

selecting a portion of the extension of the elongated member, wherein selecting the portion of the extension of the elongated member comprises determining an intersection between the bone surface and the extension of the elongated member; and determining, from the selected portion of the extension of the elongated member, trajectory data indicative of a trajectory defined by the elongated member.

2. The method of claim 1, wherein the selected portion of the extension of the elongated member is linear.

3. The method of claim 1, wherein processing the image data comprises segmenting the image data to determine second image information representative of the elongated member, and wherein the portion of the extension of the elongated member is selected based on the second image information.

4. The method of claim 1, wherein processing the image data comprises determining an endpoint of the elongated member in the bone, and wherein the selected portion of the extension of the elongated member is based on the endpoint.

5. The method of claim 4, wherein the selected portion of the extension of the elongated member comprises the endpoint and stretches over a length of the extension of the elongated member from the endpoint.

6. The method of claim 1, comprising generating display information based on the trajectory data.

7. The method of claim 6, wherein the display information is configured to visualize at least one of the trajectory and an, or the, endpoint of the elongated member in the bone.

8. The method of claim 6, wherein the display information is configured to visualize at least one of (i) the trajectory and (ii) an, or the, endpoint of the elongated member in the bone superimposed on one of (i) the image data processed to determine the extension of the elongated member and (ii) other image data representative of the bone.

9. The method of claim 6, comprising processing the image data based on the trajectory data, wherein the display information is indicative of the processed image data.

10. The method of claim 9, wherein processing the image data comprises at least one of orienting the image data and zooming into the image data.

11. The method of claim 1, comprising determining, based on the trajectory data, a cylindrical volume centered relative to the trajectory.

12. The method of claim 1, wherein the elongated member serves for placement of a cannulated screw, and comprising determining at least one screw parameter of the cannulated screw based on at least one of the image data and the trajectory data.

13. The method of claim 11, wherein the elongated member serves for placement of a cannulated screw, and comprising determining at least one screw parameter of the cannulated screw based on at least one of the image data and the trajectory data; and wherein the cylindrical volume is determined based on the at least one screw parameter and wherein, as an option, the screw is a pedicle screw and wherein the screw parameter is determined to avoid breaching.

14. The method of claim 1, wherein the trajectory defined by the trajectory data extends beyond the selected portion of the extension of the elongated member.

15. The method of claim 1, wherein the image data are representative of another elongated member placed in the, or another, bone, and comprising processing the image data to determine an extension of the other elongated member;

selecting a portion of the extension of the other elongated member;

determining, from the selected portion of the extension of the other elongated member, further trajectory data indicative of a trajectory defined by the other elongated member; and determining a relationship between the trajectories.

16. The method of claim 15, wherein the relationship comprises at least one of a distance relationship and an angular relationship.

17. A computer program product comprising program code portions to perform the steps of claim 1 when the computer program product is executed by a processor.

18. An apparatus computer system comprising one or more processors and memory storing program code for controlling operation of the one or more processors for determining a trajectory defined by an elongated member, the apparatus computer system being configured to obtain image data representative of an elongated member placed in a bone;

process the image data to determine an extension of the elongated member;

segment the image data to determine first image information representative of a bone surface;

select a portion of the extension of the elongated member, wherein selecting the portion of the extension of the elongated member comprises determining an intersection between the bone surface and the extension of the elongated member; and determine, from the selected portion of the extension of the elongated member, trajectory data indicative of a trajectory defined by the elongated member.

19. The computer system of claim 18, wherein the selected portion of the extension of the elongated member is linear.

20. The method of claim 1, wherein the elongated member is at least partially or fully flexible.

\* \* \* \* \*